United States Patent [19]

Rosenberg

[11] 4,165,376

[45] Aug. 21, 1979

[54] TREATMENT OF THE ACUTE AFTER-EFFECTS RESULTING FROM ALCOHOL INGESTION

[75] Inventor: Carl S. Rosenberg, Chicago, Ill.

[73] Assignee: Lake Shore Roentgenology, Ltd., Chicago, Ill.

[21] Appl. No.: 608,103

[22] Filed: Aug. 27, 1975

Related U.S. Application Data

[63] Continuation-in-part of Ser. No. 111,077, Jan. 29, 1971, abandoned.

[51] Int. Cl.² .......................................... A61K 31/445
[52] U.S. Cl. .................................. 424/267; 424/250; 424/253; 424/261; 424/263
[58] Field of Search ............... 424/267, 261, 253, 250, 424/251

[56] References Cited

U.S. PATENT DOCUMENTS

| | | | |
|---|---|---|---|
| 3,149,034 | 9/1964 | Ferguson | 424/263 |
| 3,160,562 | 12/1964 | Cerletti et al. | 424/261 |
| 3,218,324 | 11/1965 | Hofmann et al. | 260/285.5 |
| 3,557,287 | 1/1971 | Berde et al. | 424/253 |

FOREIGN PATENT DOCUMENTS

| | | | |
|---|---|---|---|
| 1011112 | 11/1965 | United Kingdom | 424/261 |
| 1043842 | 9/1966 | United Kingdom | 424/261 |

OTHER PUBLICATIONS

*Merck Index*, 8th ed., p. 316.
Wolff — *Headache and Other Head Pain*, 2nd ed., Oxford Univ. Press (1963) New York.

*Primary Examiner*—Frederick E. Waddell

[57] ABSTRACT

A method for the prevention of alcohol-induced thirst and/or fatigue and/or nausea, as well as other less common after-effects resulting from an excessive ingestion of alcohol. The method comprises administering an effective amount of a pharmaceutically acceptable, non-toxic member of the class of antagonists of 5-hydroxytryptamine (hereinafter referred to as 5-HT). For maximum effectiveness, the antagonist of 5-HT is administered prior to or during the onset of the acute post-alcoholic intoxication state. The indication for therapy is subjective, and the therapy is utilized pro re nata.

1 Claim, No Drawings

TREATMENT OF THE ACUTE AFTER-EFFECTS RESULTING FROM ALCOHOL INGESTION

This is a continuation-in-part of copending application Ser. No. 111,077, filed Jan. 29, 1971, now abandoned.

This invention relates to the prevention of the acute post-alcoholic intoxication state, commonly called the alcohol post-alcoholic intoxication state, commonly called the alcohol "hangover". A "hangover" results from ingesting a relatively excessive quantity of alcohol, a term understood to refer to alcoholic beverages as well as any particular alcohol found in such beverages.

More particularly, the method of the invention is concerned with the prevention of alcohol-induced thirst and/or fatigue and/or nausea by administering to a person compounds which are relatively safe and effective, competitive antagonists of 5-hydroxytryptamine (5-HT).

When a person ingests alcohol, approximately 2–10% of the ethyl alcohol contained in the beverage is excreted from the body unchanged in expired air and in the urine. The remainder of the alcohol is either oxidized or is used in synthesizing cholesterol.

Without limiting the invention as to theory, it is believed that enzymatic oxidation of an alcohol, by the enzyme alcohol dehydrogenase-linked nicotinamide-adenine-dinucleotide (NAD), the alcohol is converted to its corresponding aldehyde. This reaction occurs at a nearly constant rate, independent of the quantity of alcohol present in the body.

Each aldehyde should then undergo enzymatic oxidation to its corresponding acid by the enzyme aldehyde dehydrogenase-linked NAD. The latter oxidation may not occur at a uniform rate. It can be adversely affected either by an aldehyde directly inhibiting the oxidation of the reduced co-enzyme $NADH_2$; or, by two or more aldehydes competitively inhibiting the aldehyde dehydrogenase-linked NAD. Either effect will cause an accumulation of aldehyde to occur.

A rapid accumulation of aldehyde, within several minutes, occurs in those persons who take disulfiram, which produces the so-called "aldehyde reaction". A more prolonged accumulation of aldehyde, over several hours, is believed to provoke an acute type of inflammatory reaction which is thought to be the basic cause of the acute post-alcoholic intoxication state.

An acute type of inflammatory reaction is a tissue's nonspecific defensive mechanism against any sudden appearance of a noxious substance. It is believed that an acute type of inflammatory process is initiated whenever 5-HT is released within the tissues of an area involved with a noxious substance. The unbound 5-HT is now able to cause spasm of smooth muscle cells by occupying specific and critical receptorsites on these cells; most significantly, those smooth muscle cells in the wall of post-capillary venules within the area involved by the noxious material. An acute type of inflammatory process, therefore, is the result initiated by the unbound 5-HT. The foregoing is a somewhat simplified description, but is sufficient to facilitate an understanding of the invention.

In accordance with the concepts of this invention, alcohol-induced thirst and/or fatigue and/or nausea, the essential components of the acute post-alcoholic intoxication state, are prevented by administration of antagonists of 5-HT. In the preferred practice of this invention, use is made of 5-HT antagonists, such as cyproheptadine or the group of compounds which contain the lysergic acid radical. It has been found that the use of antagonists of 5-HT prevents or substantially minimizes the after-effects of alcohol ingestion; essentially alcohol-induced thirst, fatigue and/or nausea. The method of this invention is also effective in preventing or substantially minimizing other, less common clinical manifestations of the acute post-alcoholic intoxication state such as malaise, insomnia, drowsiness, anorexia, headache, vertigo, feelings of guilt, depression and anxiety.

The layman frequently considers the headache as the unique determining factor as to whether one does or does not have a "hangover". That assumption is false because a headache occurs only 35–40% of all acute post-alcoholic intoxication states. Even if one were to suffer from a headache, the complete absence of alcohol-induced thirst, fatigue and nausea categorically rules out the acute post-alcoholic intoxication state as defined above.

The acute post-alcoholic intoxication state reaches its full intensity several hours after a person had been drinking; when the blood level of alcohol has returned to normal. At this time, administering an antagonist of 5-HT can have no effect. The reason being that the receptor-sites would then be occupied by 5-HT, which would have initiated an acute type of inflammatory reaction.

Antagonists of 5-HT can only prevent an acute type of inflammatory process by occupying the receptor-sites prior to their occupation by 5-HT. The antagonists do not cause significant, if any, spasm of the above-mentioned smooth muscle cells. Therefore, it is mandatory to know that a release of 5-HT is to occur within the next several hours in order to receive the therapy at the proper time. Otherwise, a person would awaken during the full intensity of an acute post-alcoholic intoxication state. Thus, to be effective, antagonists of 5-HT administered in accordance with the practice of this invention should be given prior to or during the early onset of the acute after-effects of alcohol ingestion.

An antagonist cannot dislodge 5-HT from a receptor-site; nor can 5-HT dislodge an antagonist from a receptor-site. This is critically important, in that they compete for an empty receptor-site, but only the first to arrive is able to take possession of said empty receptor-site.

As stated above, aldehydes inhibit and compete for the same enzyme, i.e., aldehyde dehydrogenase-linked NAD. Were the enzyme not adversely involved, it would rapidly promote the oxidation of aldehydes to their corresponding acids in order to eliminate them from the body as end-products of the metabolism of alcohol. Thusly, an acute type of inflammatory reaction could not occur, since there would be no aldehyde accumulation to irritate tissue, which causes 5-HT to be released.

In some way, it is presumed, the reaction $$NADH_2 + O = NAD + H_2O$$

is inhibited. As a result of this inhibition, there is produced an elevated level of aldehyde in the blood, and later, in the cerebrospinal fluid. This is the result of having ingested a relatively excessive amount of alcohol.

To compare the various headaches, the vascular headaches and the migraine with the acute post-alcoholic intoxication state can be shown to be a priori incorrect.

The basic concept taught in this invention is that alcohol-induced thirst and/or fatigue and/or nausea are the sine qua non of the acute post-alcoholic intoxication state, whereas cephalagia alone is the sine qua non of the various headaches, the vascular headaches and the migraine.

As stated above, alcohol-induced thirst, fatigue and nausea are pevented by the proper medical usage of relatively safe and effective compounds which antagonize 5-HT.

There are other signs and symptoms of the acute post-alcoholic intoxication state. These include anorexia, vomiting, the need for bed-rest, difficulty in remaining fully alert and impairment of full control of physical and metal capabilities. These are non-specific signs and symptoms, and are common not only to the various headaches, the vascular headaches and the migraine, but also to the acute post-alcoholic intoxication state and many other diseases as well. Any of these signs and symptoms, taken as a group, do not logically, empirically or scientifically, relate, ipso facto, one to the other.

The art teaches that alcohol-induced thirst can be modified by increased fluid intake. In doing so, the art acknowledges, ipso facto, that said thirst does exist. The invention, on the other hand, teaches that alcohol-induced thirst, when still a potential entity, can be prevented.

The art, at present, does not teach that alcohol-induced thirst is preventable, once a sufficient quantity of alcohol as been consumed. Nor does it teach that thirst, whatever the cause, is preventable. Nor does this invention teach that any cause of thirst, except alcohol-induced thirst, is preventable; thus teaching nothing more concerning thirst.

The concept of this invention fundamentally relates to the prevention of thirst and/or fatigue and/or nausea, where they to occur as acute after-effects of alcohol ingestion (within 24 hours).

In order to fully understand the headache syndrome as a separate group of entitites, neither related to nor similar to the acute post-alcoholic intoxication state, it becomes expedient to compare them.

Several observations will be stated. Each will first present a single and simple statement thought to have objective reality concerning the various headaches, the vascular headaches and the migraine; and each in turn will be countered by a statement presently accepted as having objective reality concerning the acute post-alcoholic intoxication state:

Cephalagia, by definition, must exist in order for th various headaches, the vascular headaches and the migraine to be present, whereas cephalagia is not an essential component of the acute post-alcoholic intoxication state;

Without cephalagia, the various headaches, the vascular headaches and the migraine cannot, by definition, exist, whereas the acute post-alcoholic intoxication state occurs even though cephalagia is absent 65 to 70% of the time;

Cephalagia is the sine qua non of the various headaches, the vascular headaches and the migraine, whereas cephalagia is present in only 30 to 35% of all acute post-alcoholic intoxication states;

Thirst, per se, is not a symptom of the various headaches, the vascular headaches or the migraine, whereas thirst and/or fatigue and/or nausea, solely induced by alcohol ingestion, must be present in order for the acute post-alcoholic intoxication state to be present. They are the sine qua non of the acute post-alcoholic intoxication state, as it is defined in the specification;

Thirst, per se, is not a manifestation of the various headaches, the vascular headaches or the migraine unless it is secondary to the inability to retain fluids because of severe and continued vomiting, whereas the absence of thirst, as well as fatigue and nausea, after alcohol ingestion, rules out the presence of the acute post-alcoholic intoxication state, as it is defined in the specification;

Fatigue, per se, does not occur in the various headaches, the vascular headaches and the migraine, except after many hours and days of suffering, whereas fatigue occurs in 75 to 80% of the acute post-alcoholic intoxication state, and is probably present at the onset;

An aura often occurs minutes before the cephalagia begins in the various headaches, the vascular headaches and the migraine, whereas there is no aura involved in the acute post-alcoholic intoxication state;

Pallor often occurs during the various headaches, the vascular headaches and the migraine, whereas there is no pallor in the acute post-alcoholic intoxication state;

Sweating often occurs during the various headaches, the vascular headaches and the migraine, whereas there is no sweating during the acute post-alcoholic intoxication state;

Flushing often occurs during the various headaches, the vascular headaches and the migraine, whereas no flushing occurs during the acute post-alcoholic intoxication state;

Photophobia is very common during the various headaches, the vascular headaches and the migraine, whereas photophobia is not common in the acute post-alcoholic intoxication state;

Attacks of various headaches, vascular headaches, and migraines often occur in a quasi-random manner, although they are predictable to some extent, whereas the acute post-alcoholic intoxication state occurs hours following ingestion of alcohol and its intensity is usually dependent upon the amount and type of alcohol previously consumed;

An attack of various headaches, the vascular headaches and the migraine can begin at any time, whereas the acute post-alcoholic intoxication state is almost always present upon awakening in the morning, at which time the acute post-alcoholic intoxication state is at its highest intensity;

The various headaches, the vascular headaches and the migraine reach their full intensity usually over a period of several hours, whereas the signs and symptoms of the acute post-alcoholic intoxication state are immediately realized upon awakening, at which time they are at their highest intensity;

The various headaches, the vasular headaches and the migraine have unpredictable durations, lasting from several minutes to several days, whereas the duration of the acute post-alcoholic intoxication state is limited to 1 to 12 hours 98% of the time, and a headache need not be present;

Mental depression is not an essential symptom of the various headaches, the vascular headaches or the migraine, although it can occur after several hours as the patient develops an acute reactive depression, whereas mental depression is often present in the acute post-alcoholic intoxication state. It also is present at the beginning, not several hours later;

Feelings of guilt are not present during the various headaches, the vascular headaches and the migraine, whereas feelings of guilt are very often present during the acute post-alcoholic intoxication state;

A specific etiology of the various headaches, the vascular headaches and the migraine are less than fully understood by those skilled in the art. Numerous explanations have been published in the literature, and these have been acknowledged by the art, whereas the causal factor of the acute post-alcoholic intoxication state is well-known and obvious to one skilled in the art as well as to the laity. The casual factor is also unique and singular, i.e., excessive ingestion of alcohol;

The pathophysiology of the various headaches, the vascular headaches and the migraine is understood to be the dilitation of cranial and/or intracranial arteries, and nothing more, whereas the pathophysiology of the acute post-alcoholic intoxication state is, and may remain, essentially unknown by those who are skilled in the art;

The dilitation of certain arteries is known to be a cause of cephalagia. The dilitation has been demonstrated to respond favorably to the administration to ergotamine, whereas significant vascular dilitation, while present during the period of acute alcoholic intoxication, has not been observed during the acute post-alcoholic intoxication state, nor has ergotamine or other vasoconstrictors demonstrated any clinical effectiveness if administered during a "hangover" headache;

Inhibition of aldehyde dehydrogenase-linked NAD is absent during the various headaches, the vascular headaches and the migraine, whereas aldehyde dehydrogenase-linked NAD is markedly inhibited during the acute post-alcoholic intoxication state;

No accumulation of endogenous aldehyde occurs during the various headaches, the vascular headaches and the migraine, whereas a marked accumulation of aldehyde is known to the art to occur during the acute post-alcoholic intoxication state;

There is no significant increase or decrease in the turnover of neuroamines, such as 5-HT in the various headaches, the vascular headaches and the migraine, whereas there is a marked increase in the turnover of neuroamines, such as 5-HT during the acute post-alcoholic intoxication state;

5-HT metabolism is not affected either before, during or after an attack of the various headaches, the vascular headaches and the migraine, whereas 5-HT metabolism is markedly affected during the acute post-alcoholic intoxication state;

The urinary excretion of 5-hydroxyindole acetic acid (5-HIAA) is unchanged during the various headaches, the vascular headaches and the migraine, whereas there is a marked decrease in the urinary excretion of 5-hydroxyindole acetic acid during the acute post-alcoholic intoxication state. This is secondary to inhibition of aldehyde dehydrogenase-linked NAD;

The urinary excretion of 5-hydroxytryptophol (5-HTOL) is unchanged during the various headaches, the vascular headaches and the migraine, whereas there is a marked increase in the urinary excretion of 5-hydroxytryptophol during the acute post-alcoholic intoxication state. This is secondary to inhibition of aldehyde dehydrogenase-linked NAD;

The treatment of the various headaches, the vascular headaches and the migraine is well-known and accepted by the art, and it is based on scientific investigation, whereas the art does not consist of any method of preventing the acute post-alcoholic intoxication state. There is symptomatic therapy as well as "folk-remedies"; none are effective. They are used for relief of symptoms during the acute post-alcoholic intoxication state. The art does not teach a method of preventing the "hangover" after the alcohol has been ingested.

As indicated above, antagonists of 5-HT are well known to those skilled in the art. Preferred antagonists include compounds of the formulae:

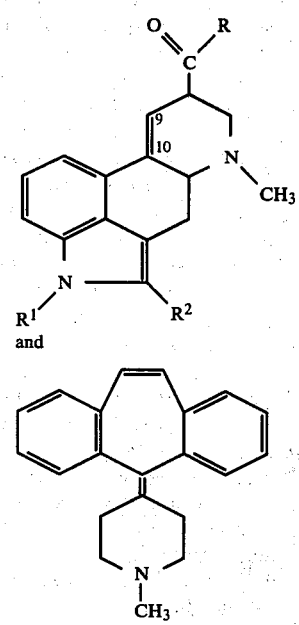

and

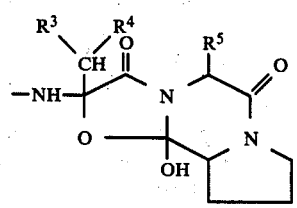

wherein R is selected from the group consisting of mono- and dialkylamino, mono-(hydroxyalkyl)amino, di-(hydroxyalkyl) amino, said alkyl and alkylene groups containing from 1 to 4 carbon atoms and the substituent wherein
$R^3$ and $R^4$ are each selected from the group consisting of H and methyl and $R^5$ is selected from the group consisting of benzyl, isopropyl and isobutyl;
$R^1$ is selected from the group consisting of H, alkyl, said alkyl containing from 1 to 4 carbon atoms;
$R^2$ is selected from the group consisting of H, Cl, Br, F and I; and the pharmaceutically-acceptable acid-addition salts thereof. These compounds can be incorporated with an inert pharmaceutical carrier or diluent.

A synergistic effect occurs when the aforesaid method concerns the administration of the shown compounds with a xanthine compound having the formula:

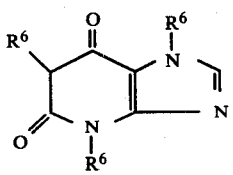

wherein each of said R groups is an alkyl group containing 1 to 4 carbon atoms. Accordingly, the therapeutic effect is believed to be enhanced by the aforesaid synergism, particularly when a xanthine is which each of said $R^6$ groups is methyl groups (caffeine), is administered orally using a dose of 100 mg to 200 mg. The generally preferred weight ratio of the 5-membered, heterocyclic nitrogen-containing compound to xanthine material is about 1:100.

Compounds which are relatively safe and effective are those in which $R^1$ and $R^2$ are hydrogen. Examples of this type include ergotamine, engonovine and methylergonovine. However, compounds which are even more preferred are those in which the $R^1$ substituent is an alkyl group. Examples of this latter type include 1-methyl-ergotamine, 1-methyl-ergonovine and 1-methylmethyl-ergotamine. Other preferred compounds used in this invention concern the 5-membered ring type wherein the 9 and 10 positions on the molecule are saturated. Other preferred compounds are those in which $R^2$ is a halide (e.g. 2-bromo-ergotamine).

The antagonists of 5-hydroxytryptamine can be administered in accordance with established methods; the oral and sublingual methods being preferred. The effective dosage generally ranges from 0.1 mg to 8.0 mgs, depending somewhat on the particular antagonist employed and the method of its administration.

The 5-membered nitrogen-containing heterocyclic compounds of this disclosure fall within the family of compounds known as the natural, synthetic and semi-synthetic amine-alkaloids and the amine-acid alkaloids, derived from the basic lysergic acid nucleus that is present in the ergot fungus.

The art teaches that the physiologically active members of this family are the dextrostereoisomers. They are arbitrarily defined by the art according to their spacial arrangement about the asymmetric carbon atoms at position 5 and position 8. In regards to the optical aspect of identification, the dextro form, be it an enantiomorph or a diastereoisomer, rotates polarized light from right to left (counter-clockwise). Therefore, the physiologically active compounds are the levorotary isomers of dextro lysergic acid. They are written either as D(−) lysergic acid or as D(l) lysergic acid. Accordingly, although the structures drawn do omit reference to configuration and physical properties, it is the levorotary dextroisomer that is contemplated herein.

Another novel aspect of this invention is that the treatment is given after or during the consumption of alcohol; but prior to, or during, the onset of the acute post-alcoholic intoxication state. All other therapy, except abstinence, concerns either the symptomatic relief of the "hangover", the treatment of addiction to alcohol, or the amelioration of complications of chronic alcoholism.

Having described the basic concepts of the invention, reference is now made to the following examples, which are provided by way of illustration and not of limitation, of the practice of the invention.

EXAMPLE 1

The following example was performed to evaluate the therapeutic value of one particular compound, ergotamine tartrate in combination with caffeine, for prevention of the acute post-alcoholic intoxication state in human beings. A series of thirty tests were performed on subjects, 23–40 years of age, after each had consumed a sufficient quantity of alcoholic beverage to cause him to feel lethargic and to admit to being intoxicated and apprehensive concerning any acute after-effects on the following morning.

Each individual had previously experienced at least one undesirable after-effect from the excess use of alcohol. Each subject was informed about and understood the test to which he was willingly subjecting himself.

The medication in each instance was two tablets, each containing ergotamine tartrate (1.0 mg) in combination with caffeine (100 mgs). A placebo, consisting of two essentially inert but similar appearing tablets, was also used. Fifteen of the subjects received the medication and fifteen of the subjects received the placebo in a random manner.

The tests were performed at a public establishment. Each individual did not know whether he was taking the medication or the placebo prior to his departure. The tablets were given to each individual by a third person, who likewise did not know which tablets were given, the tablets being contained in a small sealed envelope on which there was written only digits for use in later identification. Each subject was then interrogated by a third person the following day concerning the presence or absence of any acute after-effects upon awakening.

The data of this double blind study was tabulated and the results are set forth as follows. The symbols used have the significance as set forth below:

0: Negative (i.e., negligible)

1+: Acute post-alcoholic intoxication state lasting at least two hours

2+: Acute post-alcoholic intoxication state lasting at least six hours

3+: Acute post-alcoholic intoxication state lasting at least twelve hours

| Subject (initials) | Sex | Age | Weight | Medication | Symtoms |
|---|---|---|---|---|---|
| 1. (L.C.) | M | 40 | 220 | Placebo | 2+ |
| 2. (C.D.) | M | 39 | 195 | Placebo | 3+ |
| 3. (P.E.) | M | 28 | 170 | Medication | Negligible |
| 4. (R.P.) | M | 23 | 185 | Medication | Negligible |
| 5. (P.P.) | M | 25 | 155 | Medication | Negligible |
| 6. (F.S.) | M | 38 | 210 | Placebo | 3+ |
| 7. (J.D.) | M | 31 | 220 | Medication | Negligible |
| 8. (J.M.) | M | 29 | 195 | Medication | Negligible |
| 9. (H.M.) | M | 25 | 215 | Placebo | 3+ |
| 10. (C.R.) | M | 36 | 190 | Medication | Negligible |
| 11. (V.P.) | F | 24 | 125 | Medication | Negligible |
| 12. (S.M.) | M | 38 | 210 | Placebo | 3+ |
| 13. (J.G.) | M | 36 | 215 | Placebo | 2+ |
| 14. (C.S.) | M | 40 | 160 | Medication | Negligible |
| 15. (M.C.) | F | 31 | 130 | Medication | Negligible |
| 16. (D.L.) | F | 25 | 120 | Placebo | 3+ |
| 17. (A.W.) | F | 28 | 115 | Placebo | 2+ |
| 18. (D.B.) | F | 24 | 110 | Medication | Negligible |
| 19. (D.K.) | M | 28 | 170 | Placebo | 3+ |
| 20. (J.M.) | F | 24 | 120 | Placebo | 3+ |
| 21. (B.E.) | M | 23 | 165 | Medication | Negligible |
| 22. (J.D.) | M | 36 | 210 | Placebo | Negligible |

-continued

| Subject (initials) | Sex | Age | Weight | Medication | Symtoms |
|---|---|---|---|---|---|
| 23. (J.F.) | F | 28 | 125 | Placebo | 1+ |
| 24. (S.F.) | M | 34 | 190 | Placebo | 2+ |
| 25. (J.O'M) | F | 24 | 120 | Medication | Negligible |
| 26. (M.H.) | M | 40 | 185 | Medication | Negligible |
| 27. (K.T.) | F | 28 | 135 | Medication | Negligible |
| 28. (T.F.) | M | 31 | 170 | Placebo | 2+ |
| 29. (F.C.) | M | 36 | 165 | Placebo | 2+ |
| 30. (J.G.) | M | 31 | 180 | Medication | Negligible |

EXAMPLE 2

The procedure of Example 1 was repeated, except that the 6-member, nitrogen containing heterocyclic compound (cyproheptadine), was used with oral dosages of 8–16 mg. Comparable results were obtained.

EXAMPLE 3

The procedure of Example 1 was repeated except the following compounds, in safe and effective amounts, were used in place of ergotamine tartrate with similar results:

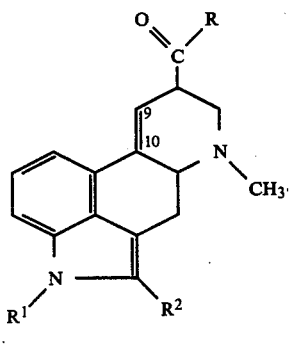

| R | R¹ | R² | acid-addition salt |
|---|---|---|---|
| —NH—CH(CH₃)₂ | H | Br | citrate |
| —NH—CH(CH₃)—CH₂OH | H | H | citrate |
| —NH—CH(CH₂CH₃)—CH₂OH | H | H | citrate |
| —NH—CH(CH₂CH₃)—CH₂—OH | —CH₃ | Cl | acetate |

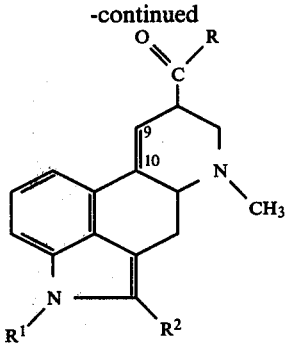

| R | R¹ | R² | acid-addition salt |
|---|---|---|---|
| C₃H₇—NH— | H | H | hydrobromide |
| —NH—CH(CH₃)—CH₂—OH | H | H | maleate |
| —NH—CH(CH₂CH₃)—CH₂OH | H | H | fumarate |
| (φ, CH₃ peptide structure) | H | H | tartrate |
| (φ, CH₃ peptide structure) | —CH₃ | H | tartrate |

| R³ | R⁴ | R⁵ | R¹ | R² | acid-addition salt |
|---|---|---|---|---|---|
| H | H | —CH(CH₃)₂ | H | H | citrate |
| —CH₃ | —CH₃ | —CH₂—CH(CH₃)₂ | CH₃ | H | citrate |

It will be understood that various changes and modifications can be made in the details of formulation and use without departing from the spirit of the invention especially as defined in the following claims.

I claim:

1. A method for treating the acute after-effects of alcohol ingestion which comprises administering to a person who had ingested alcohol an effective amount of cyproheptadine to minimize an acute inflammatory reaction from alcohol ingestion.

* * * * *